(12) United States Patent
Chappell et al.

(10) Patent No.: US 10,143,396 B2
(45) Date of Patent: Dec. 4, 2018

(54) APPARATUS FOR USE FOR PROVIDING INFORMATION ON AT LEAST ONE MUSCLE IN A PATIENT

(71) Applicant: University of Southampton, Southampton (GB)

(72) Inventors: Paul Hammond Chappell, Southampton (GB); Rodney Paul Lane, Southampton (GB)

(73) Assignee: UNIVERSITY OF SOUTHAMPTON (GB)

( * ) Notice: Subject to any disclaimer, the term of this patent is extended or adjusted under 35 U.S.C. 154(b) by 646 days.

(21) Appl. No.: 14/417,255

(22) PCT Filed: Jul. 25, 2013

(86) PCT No.: PCT/GB2013/000325
§ 371 (c)(1),
(2) Date: Jan. 26, 2015

(87) PCT Pub. No.: WO2014/016547
PCT Pub. Date: Jan. 30, 2014

(65) Prior Publication Data
US 2015/0173640 A1  Jun. 25, 2015

(30) Foreign Application Priority Data
Jul. 27, 2012  (GB) .................................. 1213592.7

(51) Int. Cl.
*A61B 5/04* (2006.01)
*A61B 5/0478* (2006.01)
(Continued)

(52) U.S. Cl.
CPC .......... *A61B 5/0478* (2013.01); *A61B 5/0482* (2013.01); *A61B 5/0531* (2013.01);
(Continued)

(58) Field of Classification Search
CPC ............................ A61B 5/0478; A61B 5/0482
(Continued)

(56) References Cited

U.S. PATENT DOCUMENTS

2004/0167420 A1  8/2004  Song et al.
2008/0171914 A1  7/2008  Ouwerkerk et al.
(Continued)

FOREIGN PATENT DOCUMENTS

CN  1381226 A  11/2002
CN  201052143 Y  4/2008
(Continued)

OTHER PUBLICATIONS

Search Report of United Kingdom Pat. App. No. GB1213592.7, dated Jun. 13, 2013, 2 pages, Intellectual Property Office, Great Britain.
(Continued)

*Primary Examiner* — Amanda Hulbert
*Assistant Examiner* — Philip C Edwards
(74) *Attorney, Agent, or Firm* — Fox Rothschild LLP (57) ABSTRACT

Apparatus for providing information on at least one muscle in a patient, which apparatus comprises: (i) signal providing means for providing measurement-enabling signals for the muscle; (ii) first contact electrodes for enabling the measurement-enabling signals from the signal providing means to be received by the patient; (iii) measurement means for measuring a parameter of the muscle, the parameter being such that it is affected by the measurement-enabling signals, and the parameter being such that it relates to at least one electrical property that is indicative of changes in tissue impedance caused by movement of the muscle; and (iv) a garment which is for being worn over the muscle in the patient and which comprises an array of separate electrically conducting areas. The apparatus optionally includes neuro-
(Continued)

muscular stimulator means for providing neuromuscular stimulation signals for the muscle.

16 Claims, 6 Drawing Sheets

(51) Int. Cl.
| | | |
|---|---|---|
| *A61B 5/053* | (2006.01) | |
| *A61B 5/0482* | (2006.01) | |
| *A61B 5/00* | (2006.01) | |

(52) U.S. Cl.
CPC .......... *A61B 5/4519* (2013.01); *A61B 5/6804* (2013.01); *A61B 5/6824* (2013.01); *A61B 5/6828* (2013.01); *A61B 2562/046* (2013.01)

(58) Field of Classification Search
USPC ........................................................ 600/388
See application file for complete search history.

(56) References Cited

U.S. PATENT DOCUMENTS

| | | | |
|---|---|---|---|
| 2009/0287102 A1 | 11/2009 | Ward | |
| 2010/0087903 A1* | 4/2010 | Van Herk | A61B 5/0531 607/115 |
| 2011/0288393 A1 | 11/2011 | Holzhacker | |

FOREIGN PATENT DOCUMENTS

| | | |
|---|---|---|
| CN | 101563056 A | 10/2009 |
| CN | 101632582 A | 1/2010 |
| CN | 101115438 B | 6/2010 |
| CN | 101237906 B | 1/2013 |
| CN | 101528282 B | 3/2013 |
| EP | 1547521 A2 | 6/2005 |
| EP | 1559371 A1 | 8/2005 |
| GB | 2473478 A | 3/2011 |
| JP | 2011010698 A | 1/2011 |
| WO | 9826714 A1 | 6/1998 |
| WO | 0105297 A2 | 1/2001 |
| WO | WO-03068076 A1 | 8/2003 |
| WO | 2007035887 A2 | 3/2007 |
| WO | 2008075250 A1 | 6/2008 |
| WO | WO-2008-075250 A1 | 6/2008 |
| WO | 2009153730 A2 | 12/2009 |
| WO | WO-2011-022068 A1 | 2/2011 |
| WO | WO-2012-006753 A1 | 1/2012 |
| WO | WO-2012/066056 A1 | 5/2012 |

OTHER PUBLICATIONS

International Preliminary Report on Patentability of PCT/GB2013/000325, dated Jan. 27, 2015, 7 pages, The International Bureau of WIPO, Geneva, Switzerland.

Kim S. C., et al., "Optimum Electrode Configuration for Detection of Arm Movement Using Bio-Impedance," Medical & Biological Engineering & Computing, Mar. 2003, pp. 141-145, vol. 41, Issue 2, Springer-Verlag.

Kim S C et al., "Optimum Electrode Configuration for Detection of Arm Movement using Bio-Impedance," Medical and Biological Engineering and Computing, vol. 41, No. 2, Mar. 1, 2003.

PCT International Search Report dated Sep. 4, 2013 for Intl. App. No. PCT/GB2013/000325, from which the instant application is based, 4 pgs.

Kim et al. "Optimum Electrode Configuration for Detection of Arm Movement Using Bio-Impedance;" Medical & Biological Engineering & Computing 2003, vol. 41, pp. 141-145.

First Notification of Office Action; issued by the State Intellectual Property Office of P.R. China, in regard to corresponding Chinese patent application Serial No. 201380046622.1; dated Jan. 11, 2017; 13 pages.

Japanese Office Action, issued by the Japanese Patent Office, in regard to corresponding Japanese patent application Serial No. 2015-523604; dated May 30, 2017; 8 pages.

European Examination Report, issued by the European Patent Office, regarding corresponding patent application Serial No. EP 13744768.6, dated Jun. 27, 2018, 6 pages.

European Examination Communication pursuant to Article 94(3) EPC, issued by the European Patent Office, regarding corresponding patent application Serial No. EP 13744768.6, dated Oct. 1, 2018; 5 pages.

* cited by examiner

APPARATUS FOR USE FOR PROVIDING INFORMATION ON AT LEAST ONE MUSCLE IN A PATIENT

RELATED APPLICATIONS

This application is a 35 U.S.C. 371 national stage filing from International Application No. PCT/GB2013/000325 filed Jul. 25, 2013 and claims priority to British Application No. 1213592.7 filed Jul. 27, 2012, the teachings of each of which are incorporated herein by reference.

FIELD OF THE INVENTION

This invention relates to apparatus for providing information on at least one muscle in a patient. The apparatus may be for providing information on the movement of the muscle in a patient suffering loss of mobility due to illness caused for example by a stroke or surgery. The apparatus may also be used for providing information on the movement of the muscle in a patient who is able bodied but who wishes to achieve better performance with better muscle movement, for example in the case of athletes. The apparatus of the present invention is primarily for use for human patients but it may also be used for animal patients.

BACKGROUND

Known apparatus for providing information on at least one muscle in a patient comprises signal providing means for providing measurement-enabling signals for the muscle, contact electrodes for enabling the measurement-enabling signals from the signal providing means to be received by the patient, and measurement means for measuring a parameter of the muscle. The known apparatus is used for giving an indication of joint articulation, for example ankle articulation. A problem with the known apparatus is that it is difficult to position the contact electrodes precisely on the required part of the patient. Variations in positioning of plus or minus 5 mm from an optimum position may adversely affect measurement results.

BRIEF SUMMARY OF EMBODIMENTS OF THE INVENTION

It is an aim of the present invention to reduce the above mentioned problem.

Accordingly, in one non-limiting embodiment of the present invention there is provided apparatus for providing information on at least one muscle in a patient, which apparatus comprises:

(i) signal providing means for providing measurement-enabling signals for the muscle;

(ii) first contact electrodes for enabling the measurement-enabling signals from the signal providing means to be received by the patient;

(iii) measurement means for measuring a parameter of the muscle, the parameter being such that it is affected by the measurement-enabling signals, and the parameter being such that it relates to at least one electrical property that is indicative of changes in tissue impedance cause by movement of the muscle; and (iv) a garment which is for being worn over the muscle in the patient and which comprises an array of separate electrically conducting areas, and the apparatus being such that the first contact electrodes are able to be positioned on the garment at a predetermined precise position for obtaining the measured parameter and with the first contact electrodes being in contact with those separate electrically conducting areas in the garment that are over the predetermined position.

The apparatus of the present invention is advantageous in that it enables the precise positioning of the first contact electrodes. This precise positioning is achievable for individual patients. Once the precise position of the first contact electrodes on the garment has been established, then the first contact electrodes are able to be secured in position on the garment, for example using securing means such for example as an adhesive. The adhesive may be an electrically conductive gel which allows adjustment repositioning of the contact electrodes prior to the electrically conductive gel curing. The initial precise positioning of the first contact electrodes on the garment may be effected by a clinician, hospital technician or other authorised person. Once the first electrodes have been secured to the garment, the garment can then be taken off after use and later put on as necessary, for example for daily use. The patient may be the person that puts the garment on and takes it off. The repeated precise positioning of the first contact electrodes is assured because they are secured to the garment. Reliable remote monitoring of the patient's muscle movement, for example from another part of the hospital or from home thus becomes possible.

The apparatus may be one in which the garment is made of a fabric which is stretchable or conformal. A garment made of such a fabric enables the garment to conform to the part of the patient's body requiring measurement of the muscle in order to indicate the movement of the muscle.

The garment may be a sleeve garment for being slid over a part of the patient. The part of the patient may be, for example an arm, a leg, a finger, a toe, a torso or a neck. The sleeve garment may be a closed loop sleeve garment which stretches in order to be placed over the part of the person.

If desired, the garment may be a strap garment for being strapped around a part of the patient. The strap garment may be in the form of an open loop which is closed by closure means. The closure means may be a fastener comprising a matrix of push to close and pull to open plastics members. One such preferred type of fastener is that known under the Registered Trade Mark Velcro. Other closure means may be employed, for example a buckle.

The array of separate electrically conducting areas may be separated by non-electrically conducting areas, or by lower electrically conducting areas. Preferably, the lower electrically conducting areas are thinner than the electrically conducting areas in order to limit current flow laterally. Usually, the electrically conducting areas in the array will be spaced apart from each other. Other types of electrically conducting areas may however be employed. The electrically conducting areas may be such that they conduct transversely through the garment but not, or not substantially, in the plane of the garment. Thus the electrically conducting areas may be regarded as being trans-conductive electrically conducting areas.

The electrically conducting areas may be woven into the garment or they may be moulded or printed into the garment.

The array may be any suitable and appropriate size and shape. Thus, for example, the array may be of a regular or irregular shape dependent upon the position and size of a muscle or muscle group being monitored or treated.

The apparatus of the present invention may be used to provide a measured parameter that only indicates movement of the muscle. The signal providing means may be a separate signal generator. There will usually be two of the first contact electrodes but more than two of the first contact electrodes may be employed if desired.

Alternatively, in addition to providing a measured parameter that indicates movement of the muscle, the apparatus of the present invention may also be used to provide neuromuscular stimulation of the muscle as determined by the indicated movement of the muscle. In this case, the apparatus of the present invention may include neuromuscular stimulator means for providing neuromuscular stimulation signals for the muscle.

When the apparatus of the present invention includes the neuromuscular stimulator means, then the signal providing means and the neuromuscular stimulator means may be provided as a single component. Alternatively, the signal providing means may be provided as a separate component from the neuromuscular stimulator means.

When the apparatus of the present invention includes the neuromuscular stimulator means, then the apparatus may be used such that the measurement-enabling signals for the muscle are imposed on the neuromuscular stimulation signals for the muscle, or vice versa.

If desired, the first contact electrodes may also enable the neuromuscular stimulation signals to be received by the patient. Alternatively, the apparatus of the present invention may include second contact electrodes which are separate from the first contact electrodes and which enable the neuromuscular stimulation signals to be received by the patient, the second contact electrodes being able to be positioned on the garment in a predetermined position for obtaining the neuromuscular stimulation and with the second contact electrodes being in contact with those separately electrically conducting areas in the garment that are over the predetermined position. When second contact electrodes are employed, there will usually by two of the second contact electrodes but more than two of the second contact electrodes may be employed if desired.

The measurement-enabling signals may have a waveform selected from at least one of:
  (a) a sine wave;
  (b) a square wave;
  (c) a triangular wave;
  (d) an arbitrary wave form shape;
  (e) repeated parts of similar or dissimilar wave forms;
  (f) a random wave form capable of being averaged; and
  (g) an impulse.
Other types of wave forms may be employed. The random wave form may be a wave form that has noise properties, for example white noise.

The measurement means may be such that it measures the parameter of the muscle by using an electrical property selected from at least one of:
  (a) phase shift;
  (b) amplitude;
  (c) slew rate;
  (d) a root mean squared value; and
  (e) impulse.
Other electrical properties may be measured if desired.

The apparatus of the present invention may include sealing means for sealing electronically conducting parts on the garment, whereby the garment is able to be cleaned. Thus, for example, after repeated use the garment may be cleaned by sponging.

The apparatus of the present invention may be used such that a clinician or other person will accurately position the first contact electrodes onto the most appropriate area of the array of separately conducting areas. The first contact electrodes may remain in place for all future uses of the garment. Alternatively, the first electrodes may be removable after a use and then be repositionable for each subsequent use. When the first electrodes are to remain in place, they may be constructed for connection to the remainder of the apparatus.

The apparatus of the present invention may be used such that the movement of the muscle is a movement caused by changes to muscle length. Other types of muscle movement may however be used.

BRIEF DESCRIPTIONS OF DRAWINGS

Embodiments of the invention will now be described solely by way of example and with reference to the accompanying drawings in which.

DETAILED DESCRIPTION OF EMBODIMENTS OF THE INVENTION

Referring to FIGS. 1-4 and 11 there is shown apparatus 2 for use for at least one muscle 4 in a patient 6. The apparatus 2 comprises signal providing means 8 for providing measurement-enabling signals for the muscle 4. The apparatus 2 also comprises two first contact electrodes 10 for enabling the measurement-enabling signals from the signal providing means 8 to be received by the patient 6.

Figure 1:
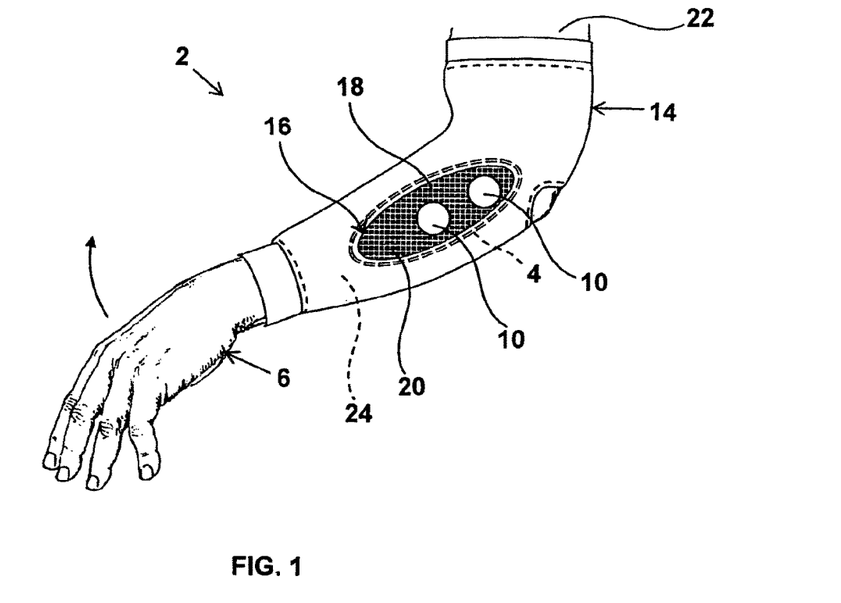
FIG. 1 shows part of first apparatus for providing information on at least one muscle in a patient, and for ensuring accurate and repeatable location of electrodes.
Figure 2:
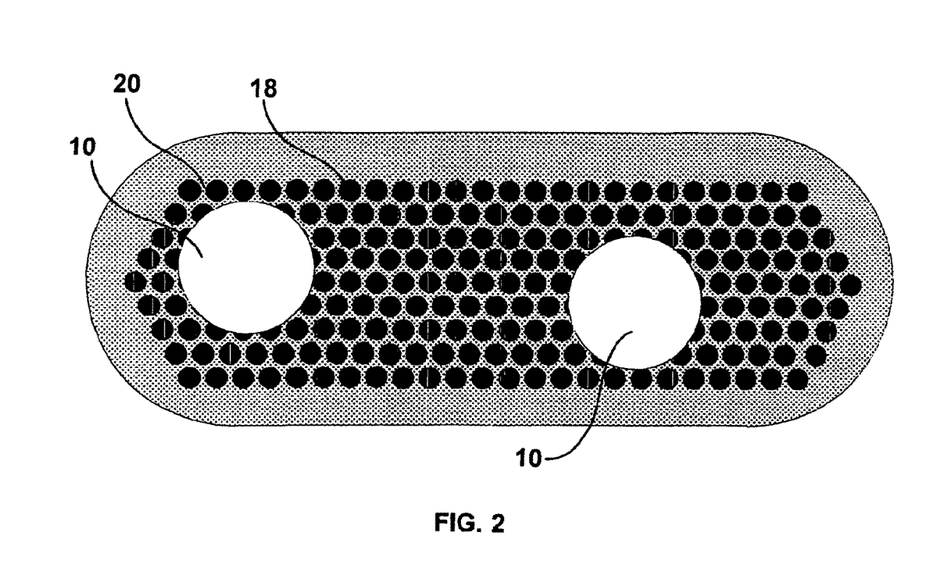
FIG. 2 is an enlarged view of part of the apparatus shown in FIG. 1.
Figure 11:
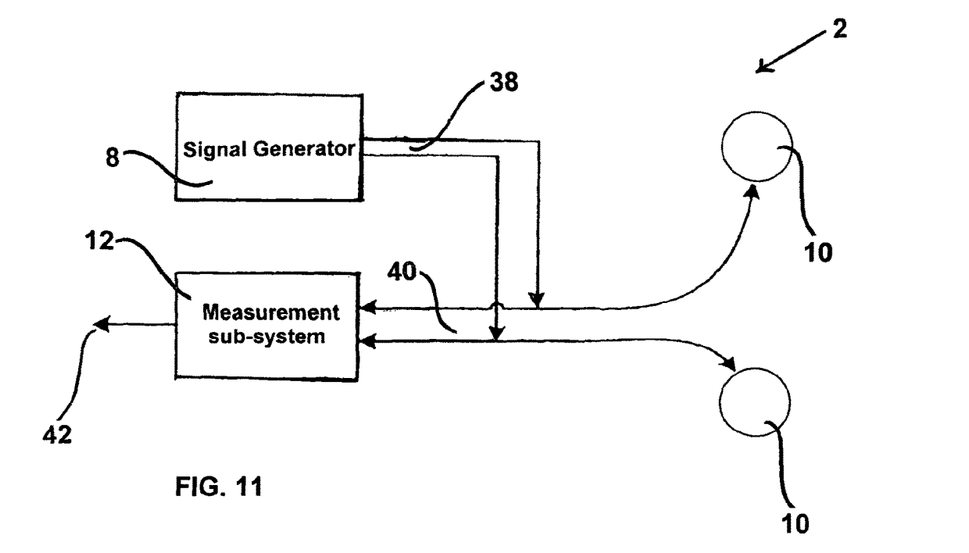
FIG. 11 shows part of first apparatus of the present invention which provides a measured parameter that indicates the movement of the muscle.

The apparatus 2 further comprises measurement means 12 for measuring a parameter of the muscle 4. The parameter is such that it is affected by the measurement-enabling signals. The parameter is such that it relates to at least one electrical property that is indicative of changes in tissue impedance caused by movement of the muscle 4.

The apparatus 2 further comprises a garment 14 which is for being worn over the muscle 4 in the patient 6. The garment 14 comprises an array 16 of separate electrically conducting areas 18 separated by non-electrically conducting areas 20.

The apparatus 2 is such that the first contact electrodes 10 are able to be positioned on the garment 14 at a predetermined precise position for obtaining the measured parameter, and with the first contact electrodes 10 being in contact with those separate electrically conducting areas 18 in the garment 14 that are over the predetermined position.

As shown in FIG. 1, the garment is a sleeve garment which is slid over an arm 22 such that the garment 14 is on a forearm 24 of the arm 22. The garment 14 is made of a fabric which is stretchable or conformable whereby the garment 14 is a sleeve garment which conforms closely to the contours of the forearm 24.

Figure 3:
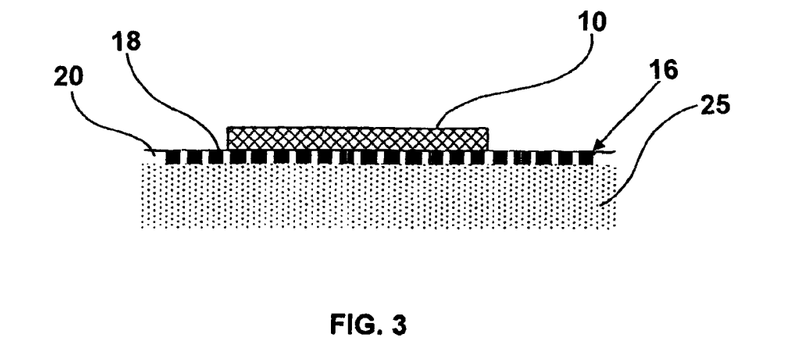
FIG. 3 is a cross section through a part of the apparatus shown in FIG. 1.
Figure 4:
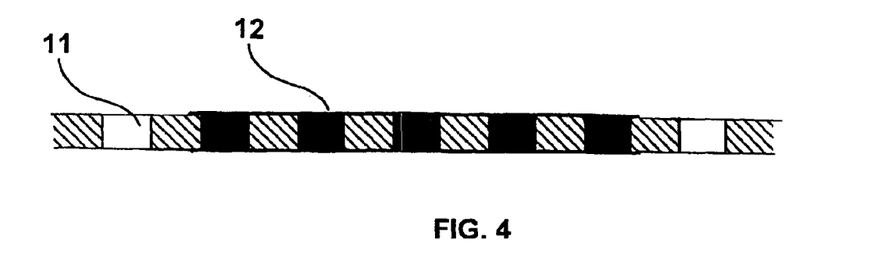
FIG. 4 is an enlarged view of part of the apparatus shown in FIG. 3.
Figure 5:
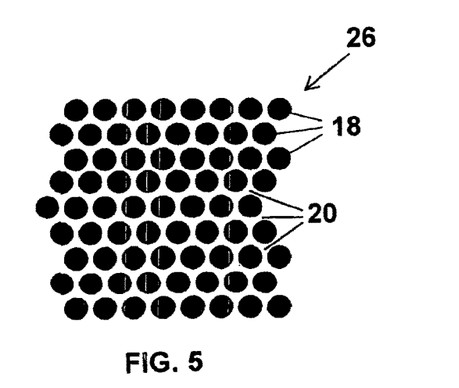
FIGS. 5-10 show different types of separate electrically conducting areas to those shown in FIG. 1.
Figure 6:
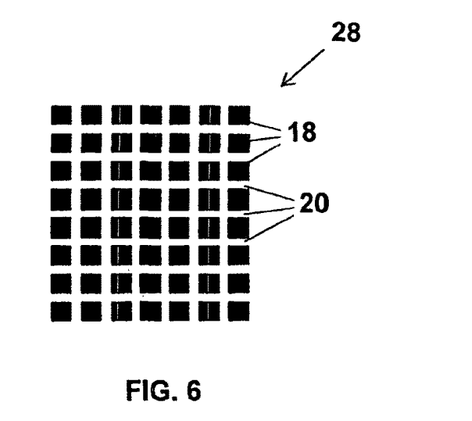
Figure 7:
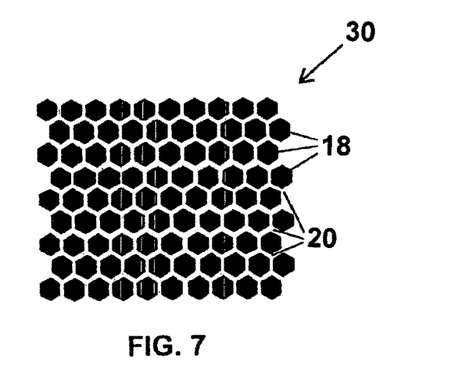
Figure 8:
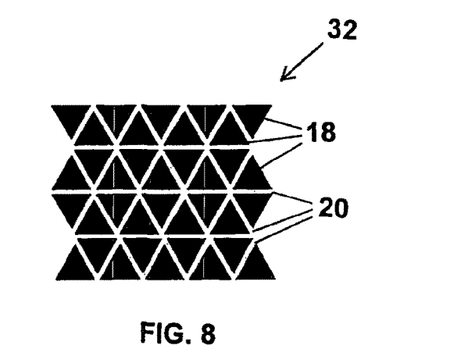
Figure 9:
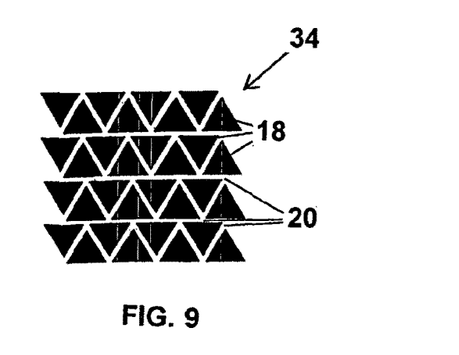
Figure 10:
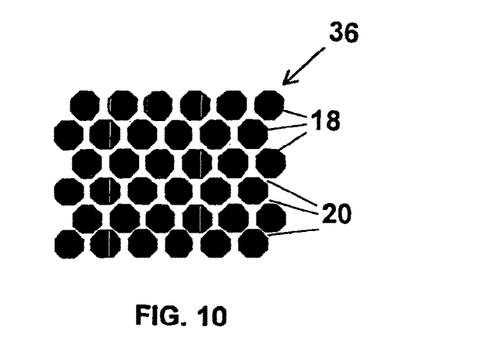

FIG. 3 shows how the matrix 16 of the electrically conducting areas 18 is able to be in contact with the skin 25 of the patient 6.

The separate electrically conducting areas 18 are regularly spaced separate electrically conducting areas 18 in the array 16. The separate electrically conducting areas 18 are woven into the garment or are moulded or printed into the garment, as can best be appreciated from FIGS. 3 and 4.

FIGS. 5-10 show six different types and/or configurations of separate electrically conducting areas 18 and surrounding non-electrically conducting areas 20 in arrays 26, 28, 30, 32, 34, 36.

FIG. 11 shows how the first apparatus 2 is such that the signal providing means 8 is a separate signal generator. In use, the signal generator 8 produces a measurement wave form 38 that creates an electrical circuit 40 through the patient's body via the first contact electrodes 10, the electrically conducting areas 18 and the measurement means 12. The measurement means 12 produces an output 42. The output 42 is thus a measured parameter that indicates movement of the muscle 4.

Figure 12:
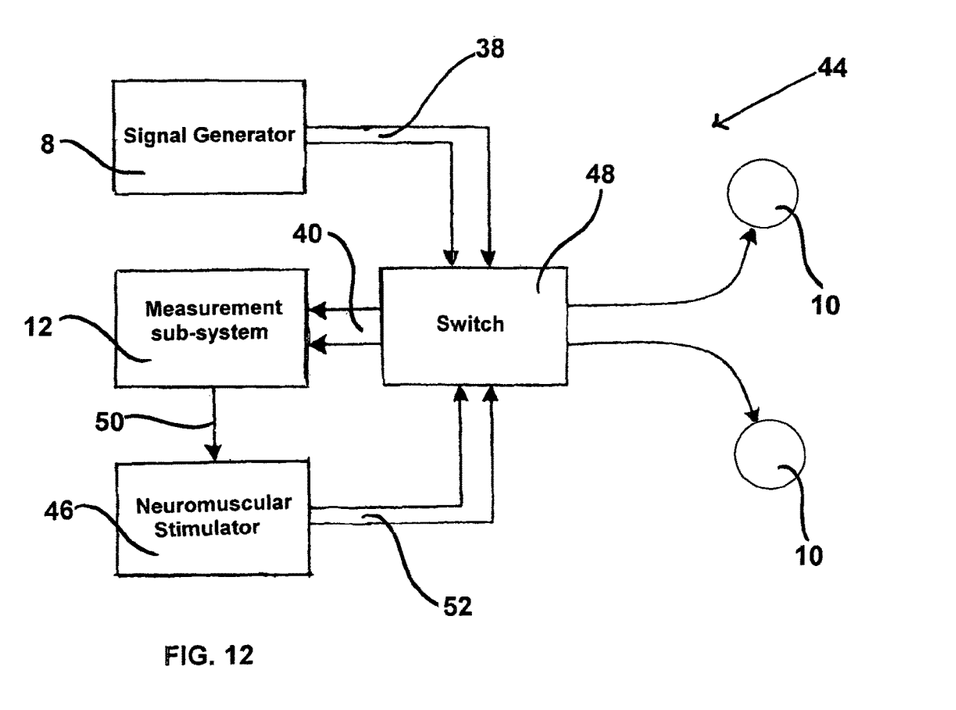
FIG. 12 shows part of second apparatus of the present invention including measurement means for indicating movement of a muscle and also neuromuscular stimulator means for providing neuromuscular stimulation signals for the muscle.

FIG. 12 shows part of second apparatus 44 of the present invention. Similar parts as in FIG. 11 have been given the same reference numerals for ease of comparison and understanding. The apparatus 44 is such that it includes neuromuscular stimulator means 46 for providing neuromuscular stimulating signals for the muscle 4. The use of the neuromuscular stimulator means is additional to the use of the signal providing means 8 as will be appreciated from FIG. 12. Thus the apparatus 44 enables the muscle 4 firstly to be measured in order to obtain an indication of the movement of the muscle 4, and secondly to receive neuromuscular stimulation signals for stimulating movement of the muscle 4. The effect of the neuromuscular stimulation can then be monitored by the measured parameter indicating the movement of the muscle 4 and the neuromuscular stimulation signals can then be adjusted accordingly for providing optimum neuromuscular stimulation for the muscle 4. The apparatus 44 operates such that the signal providing means 8 produces the wave form 38. The wave form 38 is switched by a switch 48 to form the electrical circuit 40 through the patient's body via the electrodes 10 and the measurement means 12. The calculation is made by the measurement means 12, and a control command signal 50 is then sent to the neuromuscular stimulator means 46. The neuromuscular stimulator means 46 is connected to the first contact electrodes 10 via the switch 48, and thus a stimulation pulse or pulses 52 are delivered to the first contact electrodes 10. The process is then repeated as necessary and appropriate.

Figure 13:
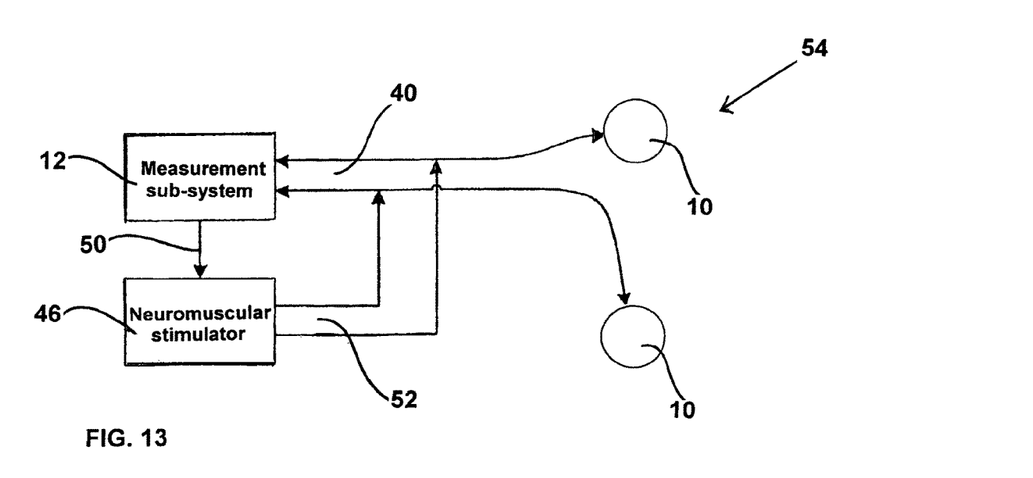
FIG. 13 shows part of third apparatus of the present invention wherein both signal providing means for providing measurement-enabling signals for the muscle and neuromuscular stimulation signals for the muscles are provided by a neuromuscular stimulator.

FIG. 13 shows third apparatus 54. Similar parts as in previous Figures have been given the same reference numerals for ease of comparison and understanding. In operation of the apparatus 54, the neuromuscular stimulator means 46 produces a neuromuscular stimulation pulse train 52 which is delivered to the first contact electrodes 10. An electrical circuit 40 is formed through the measurement means 12. The measurement means 12 calculates a control signal 50 which is sent to the neuromuscular stimulator means 46 to modulate the pulse train 52. The measurement-enabling signals are formed as a component of the neuromuscular stimulation pulse train 52. The measurement-enabling signals are generated by signal providing means 8 which are not shown in FIG. 13 but which are formed as an integral part of the neuromuscular stimulator means 46.

Figure 14:
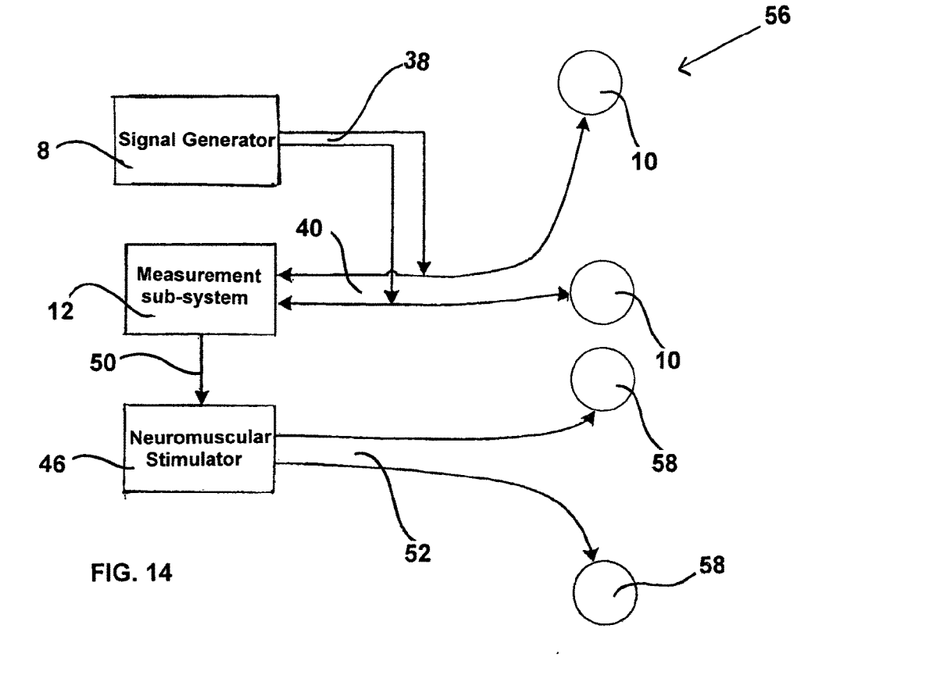
FIG. 14 shows part of fourth apparatus of the present invention, the apparatus comprising a first set of electrodes for enabling the measurement-enabling signals from the signal providing means to be received by a patient, and a second set of electrodes for receiving neuromuscular stimulation signals from neuromuscular stimulator means.

FIG. 14 shows fourth apparatus 56 of the present invention. Similar parts as in previous Figures have been given the same reference numerals for ease of comparison and understanding. The apparatus 56 is like the apparatus 44 except that the apparatus 56 employs the first contact electrodes 10 and also two second contact electrodes 58. This enables the apparatus 56 to dispense with the switch 48 used in the apparatus 44. The apparatus 56 operates such that the signal providing means 8 produces a measurement wave form 38 to form an electrical circuit 40 through the body of the patient 6 via the first contact electrodes 10 and the measurement means 12. A calculation is made by the measurement means 12, and a control command signal 50 is sent to the neuromuscular stimulator means 46. The neuromuscular stimulator means 46 delivers a stimulation pulse or pulses 52 to the second contact electrodes 58.

Figure 15:
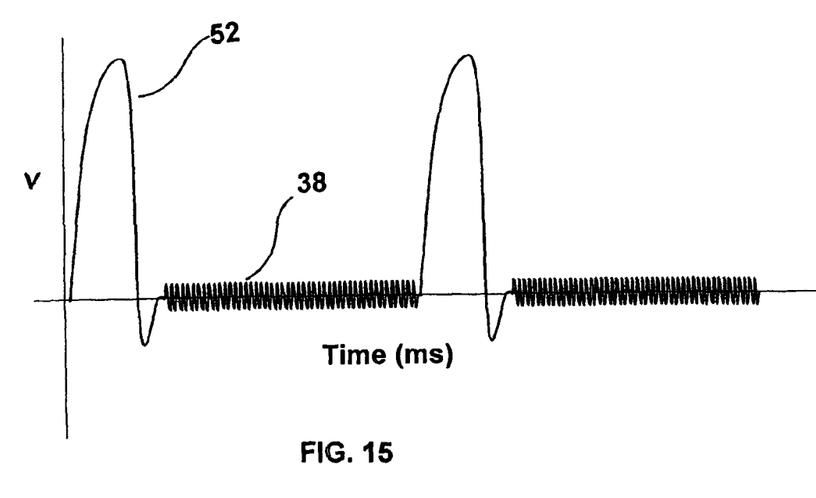
FIG. 15 shows a measurement wave form for use with a separate signal generator and neuromuscular stimulator as shown in the apparatus of FIGS. 12 and 14.

FIG. 15 shows a measurement wave form for use with a separate signal providing means 8 and a separate neuromuscular stimulator means 46, for example obtainable as shown in FIGS. 12 and 14. The neuromuscular stimulation pulses 52 are delivered with regular period. The measurement wave form 38 is applied between the stimulation pulses 52.

Figure 16:
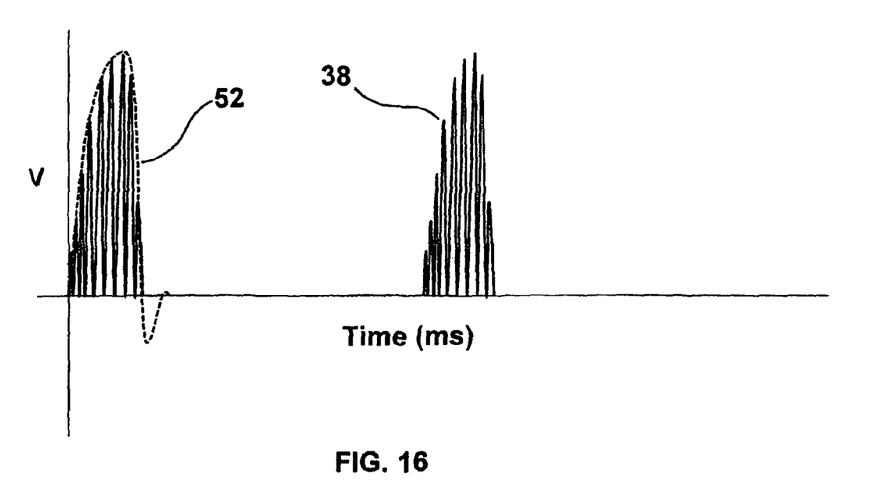
FIG. 16 shows a measurement wave form using a component of a neuromuscular stimulation wave as a measurement-enabling signal, as shown in the apparatus of FIG. 13.

FIG. 16 shows a realisation of a measurement wave form for using the component of the neuromuscular stimulation wave as may be employed using the apparatus shown in FIG. 13. The measurement wave form is delivered in modulated bursts which are delivered with the neuromuscular stimulation pulse or pulses 52.

The apparatus of the present invention may be used for control of electrical stimulation of a muscle, for example a paralysed person's arm muscle, to ensure that the muscle extends but does not over-extend and perhaps damage itself. As indicated above, advantageously the same electrodes can be used for sensing and stimulation, as sensing can occur during the sub-second pauses, for example millisecond pauses, between each stimulation pulse.

The apparatus of the present invention may be used for monitoring muscle movement and/or use, for example for:
 (a) allowing remote health physicians to remotely check that a patient is performing appropriate exercises;
 (b) helping train athletes by monitoring muscle movement during exercise;
 (c) non-optical motion-capture systems, such as for controlling the movement of a virtual avatar in a virtual environment, so the avatar matches the movement of the computer user.

The apparatus of the present invention may be cheaper to manufacture than known apparatus with angle-meters or using optical data capture. For paralysis patients, it is much easier to calibrate apparatus of the present invention to prevent over-extension, compared to systems using angle-meters, gyroscopes etc, and the apparatus of the present invention is similarly cheaper. For sports and haptics applications, one benefit is that sensors can be integral and non-obstructing within a close fitting garment, so that again the apparatus of the present invention may be cheaper and simpler than with other known systems.

The muscle fibres may enable the measurement and react as stimulated because, at a molecular scale, the shape of elongated muscle fibres may give them a greater capacitive effect than non-elongated fibres. The apparatus of the present invention may be used for therapeutic applications, for example involving electrical stimulation. Alternatively, the apparatus of the present invention may be used for non-therapeutic applications, for example measuring multiple muscle groups.

The garment may be made conductive with a conductive polymer or something similar. More than one muscle group may be monitored simultaneously. A single garment may have sensors for several muscle groups. The calibration step might be as simple as moving an arm or a joint to a position which fully extends the arm or other body part, and automatically logging the measured electrical changes to a maximum desirable predetermined value. A continuous re-calibration approach may be used if the measurement gets affected by small movements of the electrode position on an hourly basis or from day to day. Similarly, if each electrode is a close packed array of electrodes, a computer system may be employed to identify which electrode within each array has the most ideal position, based on measurements from that electrode having the greatest range of phase-lags, or some such similar method. Alternatively, in a stimulation embodiment, the apparatus of the present invention may detect which electrodes activate a muscle or joint most efficiently, and may then use these electrodes both for stimulation and sensing.

It is to be appreciated that the embodiments of the invention described above with reference to the accompanying drawings have been given by way of example only and that modifications may be effected. Thus, for example, the electrically conducting areas 18 may alternatively be separated by thinner electrically conducting areas which are in a lower plane than the electrically conducting areas 18. The apparatus 2, 44, 54, 56 may be used with more than one muscle or muscle group. The apparatus 2, 44, 54, 56 is able to be used with the garment 14, or with different types of garments for different parts of the patient's body. The patient 6 may be any suitable patient including persons suffering muscle movement impairment, or athletes. The patient 6 may alternatively be an animal, for example a dog, cat or a race horse. Individual components shown in the drawings are not limited to use in their drawings and they may be used in other drawings and in all aspects of the invention.

The invention claimed is:

1. An apparatus for providing information on at least one muscle in a patient, which apparatus comprises:
    (i) a signal generator configured to provide measurement-enabling signals for the at least one muscle;
    (ii) first contact electrodes configured to enable the measurement-enabling signals from the signal generator to be received by the patient;
    (iii) a measurement sub-system configured to measure a parameter of the at least one muscle, the parameter being affected by the measurement-enabling signals, and the parameter relating to at least one electrical property that is indicative of changes solely in muscle impedance caused by movement of the at least one muscle; and
    (iv) a garment which is for being worn over the at least one muscle in the patient and which garment comprises an array of separate electrically conducting areas that conduct transversely through the garment, each of the separate electrically conducting areas being separated by non-electrically conducting areas or by lower electrically conducting areas,
    (v) wherein the first contact electrodes are securely positionable on the garment at a predetermined precise position for obtaining the measured parameter and with the first contact electrodes being in contact with the separate electrically conducting areas in the garment that are over the predetermined position.

2. The apparatus according to claim 1 in which the garment is made of a fabric which is one or more of stretchable and conformal.

3. The apparatus according to claim 1 in which the garment is a sleeve garment for being slid over a part of the patient.

4. The apparatus according to claim 1 in which the garment is a strap garment for being strapped around a part of a person.

5. The apparatus according to claim 1 in which the electrically conducting areas are spaced electrically conducting areas in the matrix.

6. The apparatus according to claim 1 in which the electrically conducting areas are one of woven, moulded, or printed into the garment.

7. The apparatus according to claim 1 and including a neuromuscular stimulator configured to provide neuromuscular stimulation signals for the at least one muscle.

8. The apparatus according to claim 7 in which the signal generator and the neuromuscular stimulator means are provided as a single component.

9. The apparatus according to claim 7 in which the signal providing means is provided as a separate component from the neuromuscular stimulator means.

10. The apparatus according to claim 7 whereby the measurement enabling signals for the at least one muscle are imposed on the neuromuscular stimulation signals for the at least one muscle.

11. The apparatus according to claim 7 whereby the first contact electrodes also enable the neuromuscular stimulation signals to be received by the patient.

12. The apparatus according to claim 7 and including second contact electrodes which are separate from the first contact electrodes and which enable the neuromuscular stimulation signals to be received by the patient, the second contact electrodes being positionable in the garment in a predetermined position for obtaining the neuromuscular stimulation and with the second contact electrodes being in contact with the separate electrically conducting areas in the garment that are over the predetermined position.

13. The apparatus according to claim 1 in which the measurement-enabling signals have a wave form selected from at least one of:
    (a) a sine wave;
    (b) a square wave;
    (c) a triangular wave;
    (d) an arbitrary wave form shape;
    (e) repeated parts of similar or dissimilar wave forms;
    (f) a random wave form capable of being averaged; and
    (g) an impulse.

14. The apparatus according to claim 13 in which the random wave form is white noise.

15. The apparatus according to claim 1 in which the measurement sub-system is configured to measure the parameter of the at least one muscle by using an electrical property selected from at least one of:
(a) phase shift;
(b) amplitude;
(c) slew rate;
(d) a root mean squared value; and
(e) impulse.

16. The apparatus according to claim 1 and including sealing means for sealing electronically conducting parts on the garment, whereby the garment is cleanable.

* * * * *